United States Patent
Tak et al.

(10) Patent No.: US 8,142,718 B2
(45) Date of Patent: Mar. 27, 2012

(54) DISPOSABLE FOR APPLICATION IN A DEVICE FOR HEATING A PHYSIOLOGICAL FLUID

(75) Inventors: Maurice Petrus Wilhelmus Tak, Hengelo (NL); Jeroen Gerbert Hasperhoven, Bathmen (NL)

(73) Assignee: The Surgical Company International B.V., Amersfoort (NL)

( * ) Notice: Subject to any disclaimer, the term of this patent is extended or adjusted under 35 U.S.C. 154(b) by 1479 days.

(21) Appl. No.: 10/837,390

(22) Filed: Apr. 30, 2004

(65) Prior Publication Data

US 2005/0055074 A1 Mar. 10, 2005

Related U.S. Application Data

(63) Continuation-in-part of application No. PCT/NL02/00706, filed on Nov. 6, 2002.

(30) Foreign Application Priority Data

Nov. 12, 2001 (NL) ...................................... 1019347

(51) Int. Cl.
*A61M 1/00* (2006.01)
*A61M 37/00* (2006.01)
*A61F 7/00* (2006.01)

(52) U.S. Cl. ........................ 422/46; 604/6.13; 607/104

(58) Field of Classification Search ................. 604/4.01, 604/6.13, 113, 204, 317; 27/24.2; 44/46; 165/161; 607/104
See application file for complete search history.

(56) References Cited

U.S. PATENT DOCUMENTS

| 5,117,903 A | 6/1992 | Oshiyama et al. |
| 5,254,259 A * | 10/1993 | Bellhouse et al. ............ 210/650 |
| 5,381,510 A * | 1/1995 | Ford et al. ..................... 392/470 |
| 6,689,315 B2 * | 2/2004 | Linker et al. .................... 422/45 |
| 2001/0009610 A1 * | 7/2001 | Augustine et al. ............ 392/470 |
| 2001/0011585 A1 | 8/2001 | Cassidy et al. |

FOREIGN PATENT DOCUMENTS

| EP | 0253479 | * | 6/1986 |
| EP | 253479 A1 | * | 1/1988 |
| FR | 2740687 A1 | * | 5/1997 |
| GB | 2 117 101 A | | 10/1983 |

* cited by examiner

*Primary Examiner* — Leslie Deak
*Assistant Examiner* — Philip R Wiest
(74) *Attorney, Agent, or Firm* — Jeffrey D. Myers; Samantha A. Updegraff; Peacock Myers, P.C.

(57) ABSTRACT

A disposable that is suitable for application in a device for heating a physiological fluid, in particular blood, comprising a conduit for conducting fluid, which conduit comprises conduit sections that are arranged next to each other and bends that connect the conduit section, wherein at least one of the bends comprises a first turbulence-inducing obstruction.

16 Claims, 1 Drawing Sheet

DISPOSABLE FOR APPLICATION IN A DEVICE FOR HEATING A PHYSIOLOGICAL FLUID

Figure 1:
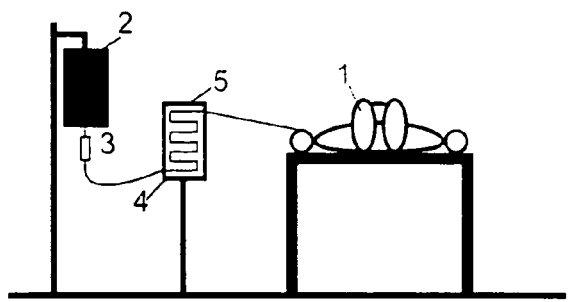

The invention relates to a disposable that is suitable for application in a device for heating a physiological fluid, in particular blood, and is provided with a conduit for conducting fluid, which conduit comprises conduit sections that are arranged next to each other and bends that connect the conduit sections.

A device for heating a physiological fluid using such a disposable is described in applicants' earlier patent application NL-A-1015999, which is not pre-published.

In such a device for heating a physiological fluid the conduit is accommodated in an element that can be exchanged after use as disposable. The conduit is further embodied such that at least one side is permeable to infrared radiation to facilitate heating by means of, for example, an infrared lamp or another source of infrared radiation.

When heating the physiological fluid in the conduit in this manner, so-called 'hot spots' should be avoided. In the case of heating blood plasma, such hot spots may cause the disintegration of the heated blood cells. The conduit through which the physiological fluid to be heated is conducted, is relatively wide and shallow, so that heating will produce only a moderate temperature gradient in the fluid.

It is the object of the invention to further improve the disposable referred to in the preamble so as to avoid the occurrence of temperature variations, in particular (but not exclusively) hot spots, and to effectively mix the physiological fluid in order to allow said fluid in the conduit to acquire a substantially uniform temperature.

This is realised in various aspects of the invention by using a disposable that complies with one or more of the appended claims.

In a first aspect of the invention the disposable is characterized in that in at least one of the bends a first turbulence-inducing obstruction is placed, preferably a baffle having a height of at least approximately 20% of the height of the conduit at the position of that baffle. Such a baffle causes a turbulence in the fluid stream such as to prevent the occurrence of hot spots. The invention is certainly not limited to a baffle of this kind, rather it is aimed at such obstructions in general that are suitable for producing sufficient turbulence. However, in order to be able to properly understand the invention, the same will be further explained with reference to the proposed use of a baffle or baffles. An important advantage of the embodiment with baffles is, moreover, that the disposable can be manufactured simply and at limited costs by injection moulding.

The first baffle (the first obstruction) is optimally effective if the same has a top edge which, viewed from the outer side of the at least one bend, slopes downward.

It is also shown to be advantageous that the first baffle is placed in the at least one bend at an angle in relation to the local direction of flow.

The effectiveness of the measures proposed in accordance with the invention is further assisted by embodying the bends succeeding the conduit sections such that their width is substantially the same as their height, and by placing the first baffle in the at least one bend near the connection with the conduit portion preceding this bend and in its extended direction. More preferably said bends are embodied with a circular cross section. This sustains the turbulence in the bends as effectively as possible.

It is further desirable to provide the disposable with a second baffle in the at least one bend.

Preferably the second baffle also has a top edge which, viewed from the outer side of the at least one bend, slopes downward, and is this second baffle also placed at an angle in the at least one bend.

Viewed in the direction of flow of the bend, the second baffle is placed after the first baffle, in a manner so as to be positioned in the curve and exactly before the part of the bend that is succeeded in its extended direction by a further conduit section.

The invention will now be further elucidated with reference to the drawing or to a non-limiting exemplary embodiment.

The drawing shows in

Figure 2:
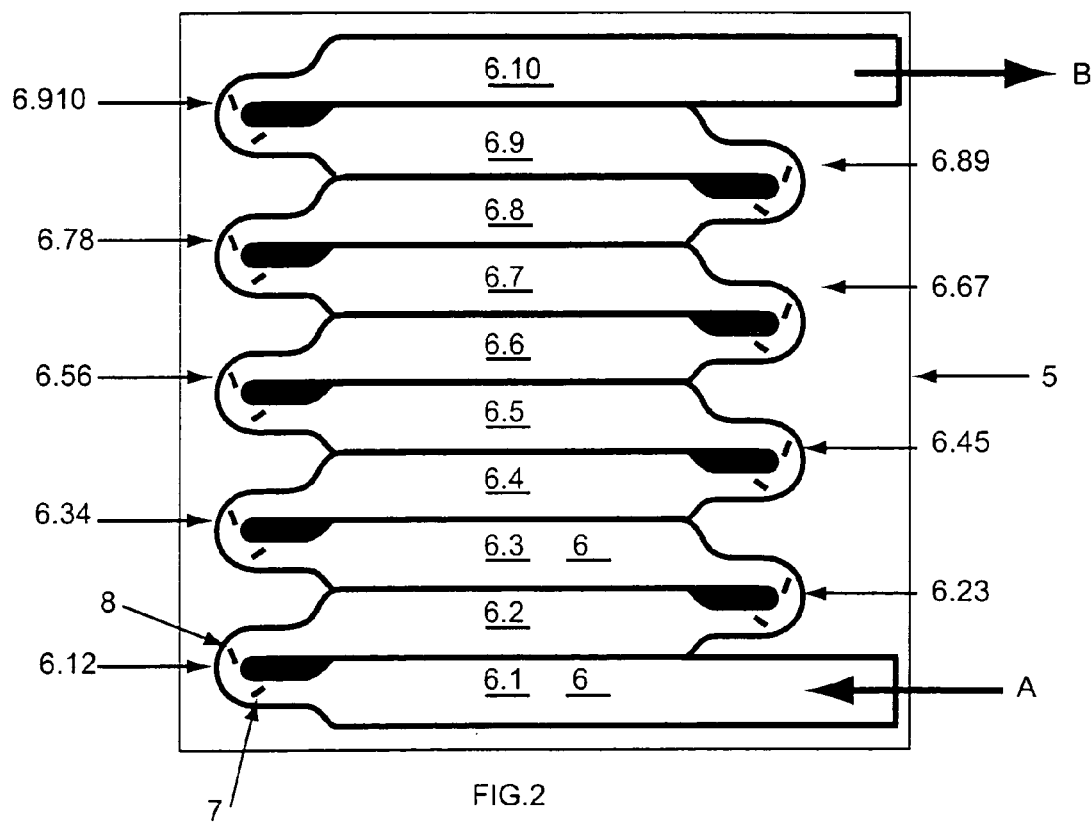
Figure 3:
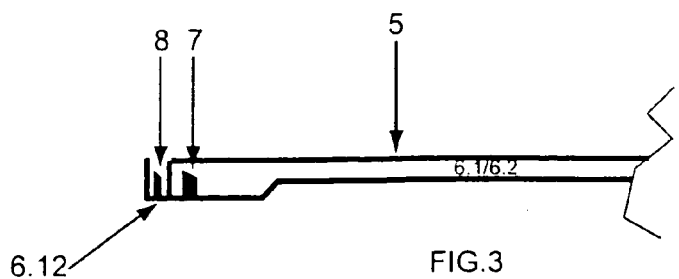

FIG. 1 a schematic illustration of the administration of blood to a patient, and FIGS. 2 and 3 in a top and side view respectively, a cross section of the disposable that can be applied in the heating device used in FIG. 1.

Identical reference numbers in the figures indicate identical parts.

Referring first to FIG. 1, a schematic illustration of blood or another physiological fluid being administered to a patient is shown. The fluid to be introduced into the body of a patient 1 is contained in a storage bag 2. Under the influence of, for example gravity, said fluid from the storage bag 2 passes a filter 3, from where it is conducted to a heating device 4 comprising a disposable 5 in which the actual heating of the fluid takes place before it is administered to the patient 1. As can be clearly seen in FIG. 2, this disposable 5 comprises a conduit 6 arranged in a flat plane. The conduit comprises conduit sections 6.1-6.10 arranged next to each other and in counterflow, and bends 6.12, 6.23, 6.34, etc., connecting the various conduit sections.

Basically, all bends are embodied the same but this is, of course, no prerequisite for the invention and it is also possible to embody just one or some of the bends in the manner explained hereafter in more detail, referring just to bend 6.12. As can be seen in FIG. 2, bend 6.12 comprises a first baffle 7 whose height, as FIG. 3 clearly shows, is approximately half that of the conduit's height at the position of the baffle 7. However, the inventors have found that a height of at least approximately 20% of the height of the conduit is also very effective.

FIG. 2 further shows that the bend 6.12 comprises a second baffle 8.

Viewed from the outside of the bend 6.12, both the first baffle 7 and the second baffle 8 preferably have top edges that slope downward. This is clearly shown in FIG. 3. FIG. 2 shows that the first baffle 7 and the second baffle 8 are placed at an angle in relation to the bulk of the local direction of flow in the bend 6.12.

FIG. 3, in combination with FIG. 2 further shows clearly that the conduit sections 6.1 and 6.2 are wide and shallow, while the bend 6.12 is embodied with a width that is substantially the same as the height, with the first baffle 7 being placed in this bend 6.12 near its connection with the conduit portion 6.1 and in its extended direction immediately preceding the bend. It is further preferred for the bends to be embodied with a circular cross section. However, is it difficult to manufacture this; in contrast, the embodiment in which the width and height of the bends are the same is easy to manufacture, while the turbulence in the bends is sustained very well.

The second baffle 8, which viewed in the direction of flow of the disposable 5 succeeds the first baffle 7, is placed in the curve of the bend 6.12, just before the portion that in its extended direction forms the succeeding conduit portion 6.2.

As will be clear from the above explanation, various modifications of the disposable elucidated with reference to the exemplary embodiment shown in the drawing are possible. This explanation merely serves to clarify the appended claims, without limiting them to the specific design of the exemplary embodiment.

What is claimed is:

1. A disposable that is suitable for application in a device for heating a physiological fluid, the disposable comprising:
   a conduit for conducting fluid, which conduit comprises conduit sections that are arranged next to each other and bends that connect the conduit sections,
   wherein the conduit sections are wide and shallow,
   wherein the bends' width is substantially the same as the bends' height,
   wherein in at least one of the bends is a first turbulence-inducing obstruction comprising a first baffle having a height of at least approximately 20% of the height of the conduit at the position of the first baffle,
   wherein the first baffle is placed in at least one bend near the connection with the conduit portion and in its extended direction, preceding this bend, and
   wherein a second baffle is provided in at least one bend.

2. A disposable according to claim 1, wherein first baffle has a top edge which, viewed from an outer side of the at least one bend, slopes downward.

3. A disposable according to claim 1, wherein first baffle is placed in the at least one bend at an angle in relation to local direction of flow.

4. A disposable according to claim 1, wherein the second baffle has a top edge which, viewed from the outer side of the at least one bend, slopes downward.

5. A disposable according to claim 1, wherein the second baffle is placed at an angle in relation to the local direction of flow in the at least one bend.

6. A disposable according to claim 1, wherein viewed in the direction of flow, the second baffle is placed after the first baffle.

7. A disposable according to claim 6, wherein the second baffle is placed in the curve of the bend before the part that is succeeded in its extended direction by a further conduit section.

8. The disposable of claim 1 wherein at least a portion of said conduit is permeable to infrared radiation.

9. An apparatus for heating a physiological fluid comprising:
   a conduit for conducting fluid, said conduit comprising sections that are arranged next to each other and bends that connect said conduit sections,
   wherein at least one turbulence-inducing obstruction is disposed within at least one of said bends,
   wherein at least a portion of said conduit is permeable to infrared radiation,
   wherein conduit sections comprise a width greater than a depth thereof, and
   wherein the bends' width is substantially the same as the bends' height.

10. The apparatus of claim 9, wherein said obstruction comprises a first baffle having a height of at least approximately 20% of the height of the conduit at the position of first baffle.

11. The apparatus of claim 10, wherein a second baffle is provided in the at least one bend.

12. The apparatus of claim 11, wherein said second baffle comprises a top edge which, when viewed from the outer side of the at least one bend, slopes downward.

13. The apparatus of claim 11, wherein said second baffle is disposed at an angle in relation to the local direction of flow in the at least one bend.

14. The apparatus of claim 11, wherein said second baffle is disposed down flow from said first baffle.

15. The apparatus of claim 9, wherein at least one of said obstructions comprises a top edge which, viewed from an outer side of said bends, slopes downward.

16. The apparatus of claim 9, wherein at least one of said obstructions is disposed in at least one bend at an angle in relation to a local direction of flow.

* * * * *